United States Patent [19]

Chittick

[11] Patent Number: 4,583,038
[45] Date of Patent: Apr. 15, 1986

[54] ELECTRICAL TESTING

[75] Inventor: Robert C. Chittick, Harlow, Great Britain

[73] Assignee: Standard Telephones and Cables, PLC, London, England

[21] Appl. No.: 471,115

[22] Filed: Mar. 1, 1983

[30] Foreign Application Priority Data

Mar. 2, 1982 [GB] United Kingdom ............... 8206030
Jun. 11, 1982 [GB] United Kingdom ............... 8217105

[51] Int. Cl.⁴ .................... H01L 7/00; G01R 31/02; G01R 31/08
[52] U.S. Cl. ..................... 324/51; 324/52; 338/34
[58] Field of Search ............. 324/51, 52, 54, 65 P, 324/439; 338/27, 34

[56] References Cited

U.S. PATENT DOCUMENTS

| | | | |
|---|---|---|---|
| 1,880,917 | 10/1932 | Eastlake | 324/54 |
| 2,742,541 | 4/1956 | Bunting | 324/65 P |
| 2,942,181 | 6/1960 | Edwards | 324/54 |
| 4,400,663 | 8/1983 | May | 324/52 |

Primary Examiner—Reinhard J. Eisenzopf
Assistant Examiner—Jose M. Solis
Attorney, Agent, or Firm—Dennis P. Clarke

[57] ABSTRACT

Insulation flaws in electrical components are detected by measurement of electrical leakage before and after immersion in a mobile ionizing solvent, e.g. a lower alkyl alcohol. A significant increase in leakage is indicative of a flaw, e.g. a crack in the insulation.

14 Claims, 2 Drawing Figures

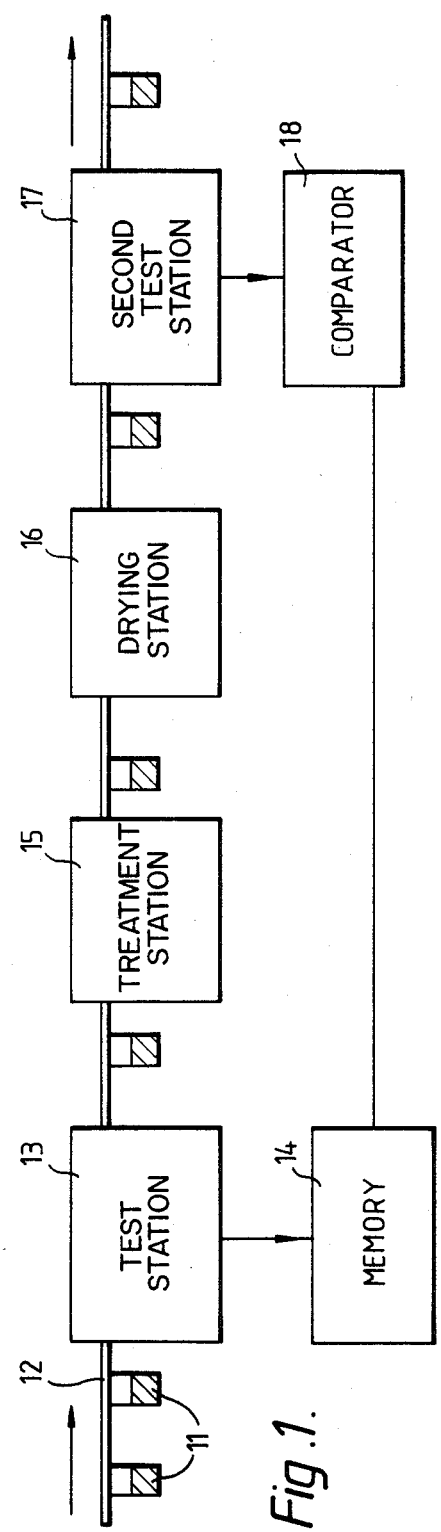
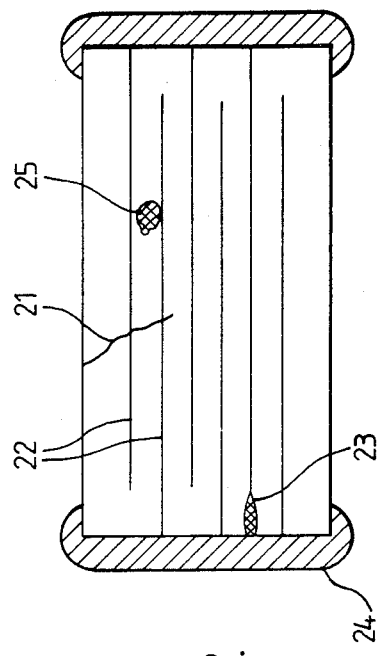

ELECTRICAL TESTING

This invention relates to testing for structural flaws such as may occur in electrical components and to techniques for improving the quality control of such components.

A major problem with the manufacture of electrical components incorporating an insulating material is that of detecting structural flaws. Such flaws may, at the time of manufacture, be only minor and thus difficult to detect but can subsequently be a cause of failure of the component. It would therefore be a considerable advantage if an incipient insulation failure could be detected by non destructive test proceedure.

For example, Ceramic dielectric capacitors, and particularly multilayer ceramic capacitors are widely used in the electronics industry as they are relatively inexpensive and have a high capacitance/volume ratio. It is usual to employ a multilayer structure when fabricating ceramic capacitors, so that layers of ceramic are interleaved with layers of metal electrode in such a way that an interdigitated two-electrode component of high capacitance value is produced. Various methods are used to make the ceramic layers as thin 'leaves', usually formed fron a mix of the finely powdered ceramic material and an organic binder solvent system. For example, in a typical conventional process, a ceramic/binder/solvent mixture is coated on to polyethylene strip, by a tape-drawing process. After drying, the ceramic/binder film is peeled off and then silk screen printed with electrodes using an ink formed from precious metal powders in an organic binder. A number of such 'leaves' are stacked and pressed together, diced, heated to remove the binder, then fired at a high temperature. End terminations and leads may be attached following normal practice and such processes as described above are well known in the art of multilayer ceramic capacitor manufacture. Following the present industry trend to decrease dielectric thickness the dielectric film integrity has assumed great importance. It is desirable to decrease the capacitor size for several reasons, mainly compatibility with micro-electronic trends and economy of materials.

A problem that has arisen with presently manufactured ceramic multilayer capacitors is that of occasional cracking of the dielectric, during the manufacturing process. This cracking provides an intrinsic breakdown path between the capacitor electrodes or between an electrode and the opposite polarity end termination and can lead to subsequent failure in service. The mechanism of this failure is not fully understood, but it is thought to involve electrochemical dissolution and migration of the internal electrode or end termination materials which then results in the formation of a low resistive breakdown path. This migration is thought to occur in those cracked regions to which there is access to the atmosphere.

In most instances cracking of the dielectric cannot be detected by visual inspection and the defect only becomes manifest after the capacitor has been in use for an extended period. It is clearly desirable to reduce such long term failures to a minimum.

Further problems arise with components packaged e.g. in an encapsulating plastics material. Again it is desirable to detect flaws in this packaging to eliminate the risk of subsequent failure.

Previous attempts to detect structural flaws have generally involved some form of electrical destructive testing on a batch basis. Such tests cannot be employed to provide 100 percent screening of components. Furthermore since they generally involve the provision of relatively costly precautions.

There are a number of approaches to component screening currently in use. One is based on the assumption that failed components have some physical defect and that the detection and removal of the defectives will eliminate low voltage failure and generally improve reliability at all voltages. The most commonly used techniques of this type are ultrasonic scanning, and crack detection by acoustic emission, both of which are used on chip capacitors. Electrical testing based on discharge techniques has also been applied to both chips and encapsulated components. Another approach is to screen out potential failures by accelerated life testing as typified by the recent MIL-C-123 procedure which specifies a test in 85% RH, 85° C. with 1.5 V dc applied. Murata et al (Proceedings of the International Symposium for Testing and Failure Analysis, 1981) use the same environment but with 1 second 1.5 V pulses. These humidity dependent tests are derived from the work of Sato et al (Proceedings of the International Symposium for Testing and Failure Analysis, 1980), who describe a test involving the measurement of insulation resistance of chip capacitors before and after extended boiling in water. These tests are time consuming and their use is likely to be limited to quality assessment on a sampling basis.

The term component as employed herein is understood to relate not only to capacitors but also to other electrical components piece parts and devices including inter alia integrated circuits, wire products and cables. The term component also includes such products as ceramic packages for integraed circuits, ceramic substrates for film circuits, and printed circuit boards.

The object of the present invention is to minimise or to overcome the disadvantages of the prior art techniques by providing a structural flaw detection process that is inexpensive, reliable and non-destructive.

According to one aspect of the invention there is provided a process for testing for a structural flaw in an electrical component, the process including subjecting the component to a volatile mobile ionising solvent, measuring a parameter associated with the electrical condition of the component, and comparing the parameter with a reference value to provide an indication of the presence of a structural flaw.

According to another aspect of the invention there is provided a process for testing for a structural flaw in a component, the process including subjecting the component to a mobile ionising solvent, measuring the electrical leakage current of the component, and comparing the leakage current with a reference value to provide an indication of the presence of a structural flaw.

According to another aspect of the invention there is provided an apparatus for measuring and testing for structural flaws in components, the apparatus including means for applying a mobile ionising solvent to the component so as to penetrate the flaw, means for measuring a parameter associated with the electrical condition of the solvent treated component, and a comparator whereby the leakage condition is compared with a reference value corresponding to the leakage condition of an untreated component.

Advantageously the process is used in the on-line testing or screening of capacitors, e.g. of the ceramic or mica type. The test may be applied at the fabrication stage to detect dielectric faults and/or at the finished stage to detect packaging faults. We have also successfully applied the technique to the testing of ceramic packages for integrated circuits.

We have found that treatment of an insulator with a mobile ionising solvent, for example a lower alkyl alcohol, provides an efficient non-destructive means for fault detection. The electrical leakage current of the insulator is measured prior to treatment with the liquid and is measured again after treatment. The two measurements are then compared. Alternatively a single measurement is made after solvent treatment and compared with a reference value. A significant increase in the leakage is indicative of the presence of one or more potentially active faults.

A variety of solvents may be used for this process. In general the solvent is of the type that produces an increase in leakage current when applied to a capacitor having a cracked dielectric or packaging defect.

An embodiment of the invention will now be described with reference to the accompanying drawings in which:

FIG. 1 is a schematic diagram of a capacitor measurement and test apparatus;

and FIG. 2 is a cross-section of a multilayer capacitor illustrating typical dielectric faults.

It should be understood that this description is by way of example only and that the techniques described herein are in no way limited to capacitor applications.

Referring to FIG. 1, capacitors 11 to be treated are mounted on a conveyor 12 and are carried through a first test station 13 where the electrical leakage of each capacitor 11 is measured and the result stored in a memory 14. The capacitors are then carried via a treatment station 15, where they are immersed in or sprayed with a mobile ionising solvent, to a drying station 16 whereby excess solvent is removed. Typically drying is effected in a current of air at ambient temperature. In some applications the capacitors may be preheated e.g. to 100° C. prior to immersion to enhance penetration by the solvent.

The treated capacitors are carried from the drying station 16 to a second test station 17. The electrical leakage current of each capacitor is again measured and is compared, via comparator 18, with the measurement for that capacitor recalled from the memory 14. If the second leakage current measurement is significantly higher than the first, i.e. the measurement differ by a predetermined magnitude, then that capacitor is directed to a reject bin. In this way ceramic capacitors, and particularly multilayer ceramic capacitors, may be screened to remove those whose dielectric is imperfect.

In a further preferred embodiment the first test station 13 is dispensed with and the leakage current of each solvent treated capacitor is compared with a reference value corresponding to the leakage of an untreated good capacitor. Those capacitors whose leakage current is significantly greater than the reference value are rejected.

In some applications a further screening of the capacitors by this technique may be effected after encapsulation. Defects in the encapsulation allow the ingress of the solvent causing a subsequent rise in leakage. Again the test process is non destructive and can thus be applied on a 100% basis.

Ceramic capacitors are of course not the only components that can be tested in this way. We have successfully applied the technique to the non-destructive testing of mica capacitors and of ceramic packages for integrated circuits.

In a typical test process a batch of 0.1 microfarad multilayer capacitors formed from an X7R dielectric were tested for electrical leakage at 10 volts. In each case the leakage current was less than or equal to $10^{-9}$ amps. The capacitors were then immersed in methanol for 10 minutes, air dried and remeasured for leakage. The majority maintained a leakage of $10^{-9}$ amps but a few showed an increase in leakage to $5 \times 10^{-9}$ amps or greater. These latter capacitors when subsequently sectioned and microscopically examined were found to exhibit dielectric cracking. Capacitors which had passed the test showed no evidence of dielectric flaws.

A variety of liquids may be employed in the technique. Typically we employ methanol, but ethanol, isopropyl alcohol, industrial methylated spirit of mixtures of any of these solvents may be used. Less advantageously water containing a wetting agent can be employed, although in certain applications the use of a wetting agent is undesirable. This list of solvents is given by way of example only and is not to be considered as limiting. Preferably the solvent should be mobile, i.e. a low viscosity and surface tension to allow rapid penetration. The solvent should also be polar and of the ionising type.

Where methanol is employed it is preferred that the water content is less than 0.1% and the conductivity is about 2 micromhos. A small trace of water is of course necessary to provide the necessary conductivity, but it has been found that all proprietary brands of methanol contain sufficient water as an impurity.

In some applications the efficiency of the solvent can be enhanced by the addition of a small quantity, e.g. 0.01%, of an ionogen or mixtures thereof. Materials of this nature, such as triethylamine, enhance the generation of ions in the solvent and hence increase the electrical conductivity.

It is preferred, although not essential, that the ionogen is relatively volatile so that subsequent removal of the material from the component can be readily effected.

The preferred liquid for testing ceramic dielectrics is methanol since it has a higher conductivity than the other alcohols and a suitably low viscosity. The relative sensitivities of the above mentioned liquids can be demonstrated by the following example. A multilayer ceramic chip capacitor had a reference value of insulation resistance equal to $10^{10}$ ohms measured 10 seconds after applying 10 VDC. The device, remeasured after 15 minutes immersion in methanol followed by surface drying, had an insulation resistance of $10^8$ ohms indicating the presence of a crack between two or more electrodes that had a path to the external environment. The corresponding values of insulation resistance after immersion in ethanol and isopropyl alcohol were $5 \times 10^8$ ohms and $5 \times 10^9$ ohms respectively. For the testing of mica capacitors or for large cracks in ceramic capacitors we prefer to employ ethyl alcohol isopropyl alcohol or mixtures thereof as, for this particular purpose, methanol can be over-sensitive.

Addition of an ionogen, e.g. triethylamine at a concentration of about 0.01% by weight, can significantly increase the conductivity of the solvent thus enhancing the sensitivity of the technique. The use of an ionogen is not however essential and we have successfully employed the technique using untreated solvents.

The mechanism of the effect is simply a shunting ff electrodes connected by a crack or other flaw by the penetrant liquid that remains in the crack after the surface liquid has evaporated. The rapid evaporation of this surface liquid is necessary to prevent masking of the effect by surface conductivity.

It has been found possible to differentiate between types of defect in multilayer ceramic chip capacitors according to the relative behaviour of the post-immersion insulation resistance and the reference value. These defects are illustrated in FIG. 2. A simple crack 21 between two opposing internal electrodes 22 will have an effect as described in the above example. The insulation resistance recovers to the reference value as the liquid evaporates from the crack. The time to recovery is dependent on the dimensions of the crack but is usually of the order of minutes.

If the defect bridging the electrodes is linked fine porosity 25, as is often the case in the Z5U dielectric, the recovery time is very long and in extreme cases there may be no noticeable recovery after several hours.

Another type of defect, known as a knit line fault 23, can also be detected. This is in effect a non-lamination of successive dielectric layers and is seen as a crack extending from one end termination 24 of the device to an internal electrode of the opposite polarity. Since the end termination material (usually silver) is normally different from the internal electrode material the result of the test has a polarity dependence. If, for example, the end termination (silver) is positive and the internal electrodes, say Palladium/silver, are negative, silver migration can readily occur in the presence of methanol along the knit line crack from the end termination and a silver dendrite can grow back from the internal electrode to the end termination. This results in an insulation resistance that decreases with time. If the polarity is reversed this rapid migration does not occur and the test behaviour is the same as that for a simple crack between internal electrodes.

The presence of these defects in capacitors with the above described test behaviour has been confirmed by destructive physical analysis. The relevance of this test with regard to multilayer ceramic capacitors is its use for example as a screening technique for potential low voltage failure. This failure mode is believed to be due to the electrochemical dissolution and migration of electrode materials under an applied d.c. electric field in the presence of atmospheric moisture and various impurities. An essential feature for the occurrence of this failure mode would then be a flaw connecting two or more opposing electrodes and a path to the outside environment from this flaw. The above procedure can detect such a flaw.

The following test procedure is a simple manual implementation that has been found suitable for 100 nF, 100 V ceramic capacitors.

1. 10 V dc is applied to the capacitor and the current ($I_1$) is measured after 10 seconds.

2. The capacitor is pre-heated to 85° C. and immersed in methanol at room temperature for a period of 15 minutes. This immersion time is not critical and can be extended indefinitely. However, immersion times of less than one minute can be insufficient to allow methanol penetration in fine cracks or porosity.

3. The capacitor is removed from the methanol, dried on a tissue and blow-dried with air at room temperature until all traces of methanol have been removed from the surface. The total drying time should be as short as possible and not exceed one minute since the methanol can evaporate from large cracks in a very short time.

4. Step 1 is repeated immediately after drying and the current ($I_2$) is measured.

A capacitor should be rejected if $I_2$ exceeds $I_1$ significantly. In practice, if a significant defect is present, then the current $I_2$ is usually greater than $10^{-8}$ amps and the ratio $I_2/I_1$ can be several orders of magnitude. In general, lower value capacitors give higher ratios for similar size defects. It is therefore possible, in the case of low value capacitors and those with a close insulation resistance tolerance, to omit step 1 and use a predetermined reference value as the failure criterion.

Table 1 illustrates the results at 2600 hours of a test at 97% RH, 85° C. on chip capacitors with 4.5 V dc across the components each with 100 kilohms representative of typical production lots but have been selected to contain a relatively large number of screen rejects. Before testing, the capacitors were subjected to a 20 hour 'burn in' at rated volts and 85° C. The 'burn in' failures, assessed as a greater than 50% drop in insulation resistance were not subjected to further life testing and are not included as screen rejects or life test failures. The insulation resistance of each capacitor was monitored throughout the test and the failure criterion was set at 500 megohms. The one failure that was not rejected by screening was tested again after removal from the life test and was found to have developed a flaw during the life test.

The failure characteristics of capacitors in accelerating environments are similar to real time failures, exhibiting both transient and permanent low insulation resistance.

TABLE 1

2600 HOUR LIFE TEST ON 100 nF CHIP CAPACITORS (97% RH, 85° C.)

| UNITS | BURN-IN | METHANOL SCREEN | LIFE TEST |
|---|---|---|---|
| 50 volt X7R 20 off | 15 pass / 5 Reject | 10 pass / 5 fail | 10 pass [100%] / 3 pass / 2 fail |
| 50 volt Z5U 20 off | 19 pass / 1 Reject | 11 pass / 8 fail | 10 pass [91%] / 1 fail* / 7 pass / 1 fail |
| 100 volt X7R 14 off | 13 pass / 1 Reject | 10 pass / 3 fail | 10 pass [100%] / 3 pass / 0 fail |

TABLE 1-continued
2600 HOUR LIFE TEST ON 100 nF CHIP CAPACITORS (97% RH, 85° C.)

| UNITS | BURN-IN | METHANOL SCREEN | LIFE TEST | |
|---|---|---|---|---|
| 100 volt Z5U 20 off | 19 pass | 9 pass | 9 pass | 100% |
| | | 10 fail | 0 pass | |
| | | | 10 fail | |
| | 1 Reject | | | |

Note:
*Failed methanol screening after life testing.

Table 2 lists the results of a life test carried out according to the MIL-C-123 test, which specifies 85° C., 85% RH 1.5 volts DC applied with a 100k series resistance to each capacitor, on two lots of resin-dipped capacitors. The test was extended to 1200 hours. Capacitors were screened by the test described herein at both the leaded chip stage and after epoxy dipping. Those included in the life test were specially selected to contain a large number of rejects from chip screening. The results of screening shown in Table 2 refer to the leaded chip stage. No screen rejects were recorded after encapsulation indicating that the test would be unlikely to detect a defective chip if the encapsulation was mechanically sound.

In this group, the capacitors were screened before the 'burn-in' and, although it is not claimed that screening will detect normal load test failures, it is worth noting that most of the burn in failures had been rejected by the chip screening. All burn-in failures were withdrawn from the life test at the burn-in stage and are not included as life test failures in Table 2.

TABLE 2
1200 HOUR LIFE TEST ON 100 VOLT 100 nF RESIN DIPPED CAPACITORS (85% RH, 85° C.)

| UNITS | METHANOL SCREEN AT CHIP STAGE* | BURN-IN AFTER ENCAPSULATION | LIFE TEST | |
|---|---|---|---|---|
| Specially selected X7R 97 off | 48 pass | 47 pass | 47 pass | 100% |
| | | | 0 fail | |
| | | 1 Reject | | |
| | 49 fail | 40 pass | 35 pass | |
| | | | 5 fail | |
| | | 9 Rejects | | |
| Specially selected Z5U 73 off | 39 pass | 39 pass | 37 pass | 95% |
| | | | 2 fail** | |
| | | 0 Rejects | | |
| | 34 fail | 26 pass | 5 pass | |
| | | | 21 fail | |
| | | 8 Rejects | | |

Note:
*All capacitors passed methanol screening after resin encapsulation.
**Failed methanol screening after life testing.

The final group, details of which are shown in Table 3, were subjected to the cylic MIL-STD-810C methanol 507.1 procedure 1 moisture resistance test with 1 volt DC applied. The capacitors, which were moulded X7R components, were measured at 5 V dc 24 hours after removal from the test environment. Owing to circuit board leakage only currents above 10 nA were considered as a failure condition. The components on this test differ from the previous two groups in that they are from normal bought-in production lots and the chips themselves are of high quality. Two of the lots had a thermoplastic encapsulant, while the remainder had the more usual thermosetting type. The failures on this test, which were predominantly in the capacitors with the thermoplastic encapsulant, were due to moisture trapped at the ceramic/encapsulant interface through which an ionic current passes between the end terminations giving rise to silver dendrite growth.

TABLE 3
MIL 810C LIFE TEST ON MOULDED CAPACITORS

| UNITS | METHANOL SCREEN | LIFE TEST | |
|---|---|---|---|
| Lot 1 thermoplastic 100 off | 1 pass | 0 pass | |
| | | 1 fail* | |
| | 100 fail | 8 pass | |
| | | 91 fail | |
| Lot 1 thermoplastic 100 off | 3 pass | 2 pass | |
| | | 1 fail* | |
| | 97 fail | 22 pass | |
| | | 75 fail | |
| Lot 3 thermoset 100 off | 100 pass | 100 pass | 100% |
| | | 0 fail | |
| | 0 fail | | |
| Lot 4 thermoset 100 off | 99 pass | 99 pass | 100% |
| | | 0 fail | |
| | 1 fail | 0 pass | |
| | | 1 fail | |
| Lot 5 thermoset 100 off | 87 pass | 86 pass | 98% |
| | | 1 fail* | |
| | 13 fail | 10 pass | |
| | | 3 fail | |
| Lot 6 thermoset 100 off | 99 pass | 98 pass | 99% |
| | | 1 fail* | |
| | 1 fail | 0 pass | |
| | | 1 fail | |

Note:
*All capacitors that passed initial methanol screening but failed life test were shown to be methanol failures on re-screening.

These examples demonstrate the feasibility of the techniques described herein for the non destructive treating of ceramic capacitors prior to use.

As previously stated, the screening test can be extended to encapsulated capacitors and other components. In the case of encapsulated devices a test failure is indicative of an encapsulant defect that allows the outside environment access to an internal defect bridging two or more of the opposing electrodes that are connected to the circuit. The bridging defect need not be within the body of the device but can be across the surface along a path formed by lack of bonding between the encapsulant and the surface of the device. This type of defect is particularly important in encapsulated multilayer ceramic capacitors with silver end terminations as silver migration can readily occur in a humid environment resulting in the growth of a shorting silver dendrite between end terminations on the ceramic surface. If the circuit impedance is sufficiently low, the heat generated when the dendrite shorts out the end terminations may even cause the encapsulation to carbonise and catch fire.

I claim:

1. A non-destructive process for testing for a dielectric structural flaw in an electrical component by measurement of an electrical leakage associated with an electrical condition of the dielectric, the process including contacting the component with a volatile mobile ionising solvent which solvent penetrates any flaw in the component, removing the component from contact with the solvent leaving residual solvent trapped in the flaw, measuring the electrical leakage of the dielectric of the treated component, and comparing the measured leakage with a reference value corresponding to an untreated component to provide an indication of the presence or absence of a structural flaw.

2. A process is claimed in claim 1, wherein the liquid is a lower aliphatic alcohol.

3. A process is claimed in claim 2, wherein the liquid is selected from the group comprising methanol, ethanol, isopropyl alcohol and mixtures thereof.

4. A process as claimed in claim 1, wherein the component is a ceramic package for an integrated circuit.

5. A process as claimed in claim 1, wherein the component is a ceramic circuit substrate.

6. An apparatus for non-destructive measuring and testing for structural flaws in a dielectric associated with an electrical component, the apparatus including means for applying a mobile ionising solvent to the component so as to penetrate any discontinuity in the dielectric, means for measuring the resistivity of an electrical leakage path associated with an electrical condition of the solvent treated component, and a comparator whereby the measured resistivity is compared with a reference value to provide an indication of the presence or absence of a structural flaw.

7. A non-destructive process for testing for a dielectric structural flaw in a capacitor, the process including contacting the capacitor with a mobile ionising solvent, removing the capacitor from contact with the solvent leaving residual solvent trapped in the flaw, measuring an electrical leakage of the capacitor, and comparing the leakage with a reference value to provide an indication of the integrity of the capacitor dielectric.

8. A process as claimed in claim 7, wherein the capacitor is a multilayer ceramic capacitor.

9. A process as claimed in claim 7, wherein the capacitor is a multilayer mica capacitor.

10. A process as claimed in claim 8, wherein the solvent is methanol.

11. A process as claimed in claim 8, wherein the solvent is selected from the group comprising isopropyl alcohol, athyl alcohol and mixtures thereof.

12. A process as claimed in claim 10, wherein said solvent contains an ionogen.

13. A process as claimed in claim 12, wherein the ionogen is triethylamine.

14. A non-destructive process for testing for dielectric and insulation flaws in a capacitor comprising a monolithic body to which encapsulation is applied, the process including contacting the capacitor both before and after encapsulation with a mobile ionising solvent, removing the capacitor from contact with the solvent leaving residual solvent trapped in the flaw, measuring an electrical leakage of the capacitor, and comparing this leakage with a reference value to provide an indication of the integrity of the capacitor dielectric and of the encapsulation.

* * * * *